United States Patent [19]

Everhart et al.

[11] Patent Number: 5,801,107

[45] Date of Patent: Sep. 1, 1998

[54] LIQUID TRANSPORT MATERIAL

[75] Inventors: Cherie Hartman Everhart, Alpharetta; Ann Louise McCormack, Cumming; Debra Nell Welchel, Alpharetta, all of Ga.

[73] Assignee: Kimberly-Clark Corporation, Neenah, Wis.

[21] Appl. No.: 777,690

[22] Filed: Dec. 20, 1996

Related U.S. Application Data

[60] Continuation of Ser. No. 467,495, Jun. 6, 1995, abandoned, which is a division of Ser. No. 72,192, Jun. 3, 1993, abandoned.

[51] Int. Cl.$^6$ ............................................. D04H 1/46
[52] U.S. Cl. .................... 442/408; 442/416; 442/417; 442/402; 442/403; 442/405
[58] Field of Search ................................. 442/381, 384, 442/387, 402, 403, 405, 408, 416, 417

[56] References Cited

U.S. PATENT DOCUMENTS

| | | | |
|---|---|---|---|
| 2,666,369 | 1/1954 | Niks | 92/38 |
| 3,042,576 | 7/1962 | Harmon et al. | 162/114 |
| 3,081,500 | 3/1963 | Griswold et al. | 19/161 |
| 3,081,515 | 3/1963 | Griswold et al. | 28/78 |
| 3,220,914 | 11/1965 | Boadway et al. | 161/128 |
| 3,284,857 | 11/1966 | Hynek | 19/161 |
| 3,471,907 | 10/1969 | Beckers | 26/18.6 |
| 3,477,906 | 11/1969 | Rabstad | 162/205 |
| 3,485,706 | 12/1969 | Evans | 161/72 |
| 3,498,874 | 3/1970 | Evans et al. | 161/109 |
| 3,565,756 | 2/1971 | Kashiwabara et al. | 162/297 |
| 3,750,237 | 8/1973 | Kalwaites | 19/161 P |
| 3,821,068 | 6/1974 | Shaw | 162/111 |
| 4,109,353 | 8/1978 | Mitchell et al. | 28/104 |
| 4,128,686 | 12/1978 | Kyle et al. | 428/234 |
| 4,166,877 | 9/1979 | Brandon et al. | 428/221 |
| 4,190,695 | 2/1980 | Niederhauser | 428/234 |
| 4,228,123 | 10/1980 | Marshall | 264/557 |
| 4,329,763 | 5/1982 | Alexander et al. | 28/104 |
| 4,440,597 | 4/1984 | Wells et al. | 162/111 |

(List continued on next page.)

FOREIGN PATENT DOCUMENTS

| | | |
|---|---|---|
| 841938 | 5/1970 | Canada . |
| 128667 | 12/1984 | European Pat. Off. . |
| 308320 | 3/1989 | European Pat. Off. . |
| 333228 | 9/1989 | European Pat. Off. . |
| 411752 | 2/1991 | European Pat. Off. . |
| 483816 | 5/1992 | European Pat. Off. . |
| 492554 | 7/1992 | European Pat. Off. . |
| 540041 | 5/1993 | European Pat. Off. . |
| 2080699 | 3/1990 | Japan . |
| 1212473 | 11/1970 | United Kingdom . |
| 91/11162 | 8/1991 | WIPO . |
| 91/11163 | 8/1991 | WIPO . |
| 91/11165 | 8/1991 | WIPO . |
| 93/20272 | 10/1993 | WIPO . |

OTHER PUBLICATIONS

"Aspects of Jetlace Technology as Applied to Wet–Laid Non–Wovens", Nonwovens Conference, Nov. 1987.
"Wires for Hydroentanglement Systems", Nonwoven Fabrics Forum, Jun. 1988.
"Hydroentanglement Technology Applied to Wet–Formed and Other Precursor Webs", TAPPI Journal, Jun. 1990.

Primary Examiner—Marion E. McCamish
Assistant Examiner—Elizabeth M. Cole
Attorney, Agent, or Firm—Karl V. Sidor

[57] ABSTRACT

Disclosed is a liquid transport material composed of a pulp fibers hydraulically needled into a nonwoven fibrous structure adapted to have a liquid transport value of at least 12 grams of liquid per gram of material over 30 minutes. The liquid transport material may contain up to about 50 percent, by weight, short staple length fibers as well as effective amounts of various particulates. The liquid transport material may be used as a liquid transport component of an absorbent structure which may be part of, for example, a personal care product. Also disclosed is a process of making a liquid transport material utilizing hydraulic needling techniques.

17 Claims, 4 Drawing Sheets

U.S. PATENT DOCUMENTS

| | | | |
|---|---|---|---|
| 4,542,060 | 9/1985 | Yoshida et al. | 428/287 |
| 4,623,575 | 11/1986 | Brooks et al. | 428/113 |
| 4,665,957 | 5/1987 | Suzuki et al. | 141/39 |
| 4,693,922 | 9/1987 | Buyofsky et al. | 428/134 |
| 4,695,500 | 9/1987 | Dyer et al. | 428/134 |
| 4,735,842 | 4/1988 | Buyofsky et al. | 428/134 |
| 4,755,421 | 7/1988 | Manning et al. | 428/224 |
| 4,810,568 | 3/1989 | Buyofsky et al. | 428/284 |
| 4,883,709 | 11/1989 | Nozaki et al. | 428/288 |
| 4,920,001 | 4/1990 | Lee et al. | 428/289 |
| 4,931,355 | 6/1990 | Radwanski et al. | 428/283 |
| 4,939,016 | 7/1990 | Radwanski et al. | 428/152 |
| 4,959,894 | 10/1990 | Jeffers et al. | 28/104 |
| 5,009,747 | 4/1991 | Viazmensky et al. | 162/115 |
| 5,137,600 | 8/1992 | Barnes et al. | 162/115 |
| 5,238,644 | 8/1993 | Boulanger et al. | 264/557 |
| 5,284,703 | 2/1994 | Everhart et al. | 428/283 |

LIQUID TRANSPORT MATERIAL

This application is a continuation of application Ser. No. 08/467,495, abandoned, entitled "Liquid Transport Material" and filed in the U.S. Patent and Trademark Office on Jun. 6, 1995, which is a divisional of application Ser. No. 08/072,192, abandoned, entitled "Liquid Transport Material" and filed in the U.S. Patent and Trademark Office on Jun. 3, 1993. The entirety of this application is hereby incorporated by reference.

FIELD OF THE INVENTION

The present invention relates to a nonwoven fibrous material and a process of making the same.

BACKGROUND OF THE INVENTION

Generally speaking, nonwoven webs made from pulp fibers and/or mixtures of pulp fibers and other fibrous materials have long been known to be useful absorbers of liquids. In some cases, these nonwoven webs have been known to draw up liquid and distribute it throughout the web. Such webs can be incorporated in products intended to absorb liquids.

Superabsorbent materials are also known to be useful in products intended to absorb liquids. These materials are most often found in powder or particulate form and may be used to improve the performance of personal care products such as, for example, diapers. Superabsorbent materials have, in the past, been mixed into fibrous webs such as, for example, pulp fluff webs or incorporated into laminate structures.

Superabsorbent materials have enabled the design and manufacture of thin absorbent structures having desirable absorbent performance of much bulkier pulp fluff structures. Such thin absorbent structures have been used to improve the fit of personal care products which, in turn, enhances comfort and protection against leaks. It would be desirable to produce even thinner absorbent structures by increasing the proportion of superabsorbent material in the absorbent structure. In addition, thinner absorbent structures can greatly reduce the volume of material requiring disposal once a product containing such an absorbent structure has been used.

Unfortunately, when superabsorbent materials are added to pulp fluff webs or incorporated into absorbent structures, the superabsorbents have a tendency to reduce the liquid distribution properties of the webs or laminates. Usually, this occurs in the form of gel-blocking. When superabsorbents absorb liquid, they typically swell and form a gel-like material that hinders the passage of liquid through the formerly powdery or particulate material. Thus, the portions of these thin absorbent structures which first contact liquid can form a gel-like material that blocks the transfer of liquid to other portions of the absorbent structure. This undesirable phenomena appears to increase as the proportion of superabsorbent in the absorbent structure is increased. Gel-blocking can also reduce the ability of an absorbent structure to handle consecutive applications of liquid. For example, a thin absorbent structure having adequate absorbent capacity could absorb a first application of a liquid yet fail to satisfactorily absorb later applications of liquid if the unused superabsorbent is sealed off by gel-blocking.

While various absorbent structures that contain superabsorbent materials are known, those structures generally fail to adequately address problems associated with capturing and transporting liquid throughout an absorbent structure and then releasing that liquid to superabsorbent materials to make efficient use of all the superabsorbent materials. For example, some absorbent structures contain liquid distribution materials that readily absorb and wick liquid. However such materials typically have difficulty releasing liquid to the superabsorbent. Thus, there is still a need for an effective and efficient liquid transport material. Since absorbent structures are often part of disposable personal care products, it is important that the liquid transport material also be inexpensive. Also, there is still a need for an effective absorbent structure which incorporates an inexpensive and efficient liquid transport material.

DEFINITIONS

The term "hydraulically needled liquid transport material" as used herein refers to a nonwoven fibrous web containing a network of fibers that has been loosened and rearranged by treatment with relatively low energy jets of fluid (i.e., hydraulic needling) so that the web is adapted to absorb, transport and release liquid to an absorbent material at a rate at least about 12 grams of liquid per gram of material. Generally speaking, hydraulic needling loosens and rearranges fibers in a nonwoven web without adding substantial strength to the web as is found in techniques such as, for example, hydraulic entangling.

As used herein, the term "liquid transport value" refers to the volume of liquid which can be transported by a material from a liquid reservoir and delivered to an absorbent system set up a specified distance above the liquid reservoir. A liquid transport value serves as a measure of the ability of a material to function as a "pipeline" for liquid. Liquid transport value is determined utilizing a Distribution/Retention Fluid Transfer Test. In this test, a reservoir of liquid is placed on an electronic balance which is linked to a data acquisition system. A variety of liquids and liquid mixtures may be used depending on the application of the material. Typically, liquids such as, for example, water, saline solution or synthetic urine are used. Unless otherwise specified, the liquid transport values reported herein were determined utilizing synthetic urine (synthetic urine Item No. K-C 399105 available from PPG Industries). A highly absorbent material (eg., a layer of superabsorbent) is placed in a container above the reservoir such that the distance between the absorbent and the liquid corresponds to the desired test height. The distribution material to be tested is suspended vertically between the reservoir and the absorbent material. Contact area between the absorbent and distribution material is held constant, and is placed under a specified pressure (e.g. 0.25 psi). Delivery heights and absorbent media may be varied as appropriate in order to evaluate different materials. Unless otherwise specified, the liquid transport values described herein are measured utilizing a delivery height of about 10 centimeters (about 4 inches). Typically, material tested has a width of about 5 centimeters (about 2 inches) in the cross-machine direction and the contact area with the absorbent is generally about 5×5 centimeters (about 2×2 inches). Length of the distribution material sample depends upon the height at which the test will be conducted. For a test height of 10 centimeters (about 4 inches), a sample length of about 18 centimeters (about 7 inches) is appropriate. This allows for approximately 2.5 centimeters (about 1 inch) of the sample to extend into the reservoir. The balance will measure weight loss by the reservoir as uptake by the distribution material. The weight loss (i.e., fluid movement) over time is recorded by the data acquisition system. The length of the test can vary. A test of about 30 minutes is usually adequate to evaluate the liquid transport value of the material. In some cases, a test lasting about 60 minutes may be used. At the conclusion of the test, both the absorbent and distribution materials are reweighed and rebulked to determine the balance of fluid movement, and to account for fluid loss. Loss due to evaporation can vary based on reservoir surface area and relative humidity, but when testing conditions vary little, this loss can be ignored. Data can be normalized to account for differences in the basis weight of liquid material and/or length of testing.

The term "pulp" as used herein refers to cellulose containing fibers from natural sources such as woody and non-woody plants. Woody plants include, for example, deciduous and coniferous trees. Non-woody plants include, for example, cotton, flax, esparto grass, milkweed, straw, jute hemp, and bagasse.

The term "average fiber length" as used herein refers to a weighted average length of pulp fibers determined utilizing a Kajaani fiber analyzer model No. FS-100 available from Kajaani Oy Electronics, Kajaani, Finland. According to the test procedure, a pulp sample is treated with a macerating liquid to ensure that no fiber bundles or shives are present. Each pulp sample is disintegrated into hot water and diluted to an approximately 0.001% solution. Individual test samples are drawn in approximately 50 to 100 ml portions from the dilute solution when tested using the standard Kajaani fiber analysis test procedure. The weighted average fiber length may be expressed by the following equation:

$$\sum_{x_i=0}^{k} (x_i * n_i)/n$$

where k=maximum fiber length
$x_i$=fiber length
$n_i$=number of fibers having length $x_i$
n=total number of fibers measured.

The term "low-average fiber length pulp" as used herein refers to pulp that contains a significant amount of short fibers and non-fiber particles which may yield relatively tight, impermeable paper sheets or nonwoven webs that are less desirable in applications where absorbency and rapid fluid intake are important. Many secondary wood fiber pulps may be considered low average fiber length pulps; however, the quality of the secondary wood fiber pulp will depend on the quality of the recycled fibers and the type and amount of previous processing. Low-average fiber length pulps may have an average fiber length of less than about 1.2 mm as determined by an optical fiber analyzer such as, for example, a Kajaani fiber analyzer model No. FS-100 (Kajaani Oy Electronics, Kajaani, Finland). For example, low average fiber length pulps may have an average fiber length ranging from about 0.7 to 1.2 mm. Exemplary low average fiber length pulps include virgin hardwood pulp, and secondary fiber pulp from sources such as, for example, office waste, newsprint, and paperboard scrap.

The term "high-average fiber length pulp" as used herein refers to pulp that contains a relatively small amount of short fibers and non-fiber particles which may yield relatively open, permeable paper sheets or nonwoven webs that are desirable in applications where absorbency and rapid fluid intake are important. High-average fiber length pulp is typically formed from non-secondary (i.e., virgin) fibers. Secondary fiber pulp which has been screened may also have a high-average fiber length. High-average fiber length pulps typically have an average fiber length of greater than about 1.5 mm as determined by an optical fiber analyzer such as, for example, a Kajaani fiber analyzer model No. FS-100 (Kajaani Oy Electronics, Kajaani, Finland). For example, a high-average fiber length pulp may have an average fiber length from about 1.5 mm to about 6 mm. Exemplary high-average fiber length pulps which are wood fiber pulps include, for example, bleached and unbleached virgin softwood fiber pulps.

The term "vertical wicking rate" as used herein refers to the rate at which water is drawn in the vertical direction by a strip of an absorbent material. The vertical wicking rate was determined for a pre-weighed sample of absorbent material (having a machine direction length of about 12 inches and a cross-machine direction width of about 3 inches) by lowering the end of the sample about 0.25 inches (about 1 cm) into synthetic urine (synthetic urine Item No. K-C 399105 available from PPG Industries). The sample is fixed in a vertical position with one end in the synthetic urine, and the distance the liquid wicks along the machine direction of the sample is measured after an interval of about 15 minutes. The sample is then removed from the solution and weighed to measure the wicking pickup, that is, the amount of liquid absorbed by the sample during the vertical wicking test.

The term "porosity" as used herein refers to the ability of a fluid, such as, for example, a gas to pass through a material. Porosity may be expressed in units of volume per unit time per unit area, for example, (cubic feet per minute) per square foot of material (e.g., ($ft^3$/minute/$ft^2$) or (cfm/$ft^2$)). The porosity was determined utilizing a Frazier Air Permeability Tester available from the Frazier Precision Instrument Company and measured in accordance with Federal Test Method 5450, Standard No. 191A, except that the sample size was 8"×8" instead of 7"×7".

The term "mean flow pore size" as used herein refers to a measure of average pore diameter as determined by a liquid displacement techniques utilizing a Coulter Porometer and Coulter POROFIL™ test liquid available from Coulter Electronics Limited, Luton, England. The mean flow pore size is determined by wetting a test sample with a liquid having a very low surface tension (i.e., Coulter POROFIL™). Air pressure is applied to one side of the sample. Eventually, as the air pressure is increased, the capillary attraction of the fluid in the largest pores is overcome, forcing the liquid out and allowing air to pass through the sample. With further increases in the air pressure, progressively smaller and smaller holes will clear. A flow versus pressure relationship for the wet sample can be established and compared to the results for the dry sample. The mean flow pore size is measured at the point where the curve representing 50% of the dry sample flow versus pressure intersects the curve representing wet sample flow versus pressure. The diameter of the pore which opens at that particular pressure (i.e., the mean flow pore size) can be determined from the following expression:

$$\text{Pore Diameter } (\mu m)=(40\tau)/\text{pressure}$$

where τ=surface tension of the fluid expressed in units of mN/M; the pressure is the applied pressure expressed in millibars (mbar); and the very low surface tension of the liquid used to wet the sample allows one to assume that the contact angle of the liquid on the sample is about zero.

The term "bulk density" as used herein refers to the weight of a material per unit of volume. Bulk density is generally expressed in units of weight/volume (e.g., grams per cubic centimeter). The bulk density of flat, generally planar materials such as, for example, fibrous nonwoven webs, may be derived from measurements of thickness and basis weight of a sample. The thickness of the samples is determined utilizing a Model 49-70 thickness tester available from TMI (Testing Machines Incorporated) of Amityville, N.Y. The thickness was measured using a 2-inch diameter circular foot at an applied pressure of about 0.2 pounds per square inch (psi). The basis weight of the sample was determined essentially in accordance with ASTM D-3776-9 with the following changes: 1) sample size was 4 inches×4 inches square; and 2) a total of 9 samples were weighed.

The term "specific volume" as used herein refers to the inverse bulk density of a material (i.e., volume per unit of weight) and may be expressed in units of cubic centimeters per gram.

The term "machine direction" as used herein refers to the direction of travel of the forming surface onto which fibers are deposited during formation of a nonwoven web.

The term "cross-machine direction" as used herein refers to the direction which is perpendicular to the machine direction defined above.

The term "mechanical softening" as used herein refers to softening imparted to a sheet of material by a mechanical process. Exemplary mechanical processes which may be used to soften a sheet of material include calendering, perforating, aperturing, perf-embossing, embossing, pattern embossing, differential drawing, creping and rollers.

The term "superabsorbent" as used herein refers to absorbent materials capable of absorbing at least 10 grams of aqueous liquid (e.g. water, saline solution or synthetic urine Item No. K-C 399105 available from PPG Industries) per gram of absorbent material while immersed in the liquid for 4 hours and holding the absorbed liquid while under a compression force of up to about 1.5 pounds per square inch.

SUMMARY OF THE INVENTION

The present invention addresses the needs discussed above by providing a liquid transport material composed of pulp fibers hydraulically needled into a nonwoven fibrous structure so that the material is adapted to have a liquid transport value of at least 12 grams of liquid per gram of material over 30 minutes. Desirably, the liquid transport material has a liquid transport value of at least about 15 grams of liquid per gram of material over 30 minutes. More desirably, the liquid transport material has a liquid transport value ranging from about 17 to about 25 grams of liquid per gram of material over 30 minutes. According to one aspect of the invention, the liquid transport material may have a specific volume ranging from about 8 to about 15 cm³/g and/or a vertical wicking height of at least about 18 cm per 15 minutes.

According to the one embodiment of the present invention, the pulp fibers of the liquid transport material may be high-average fiber length pulp fibers. For example, the pulp fibers may have an average fiber length from about 2 to about 5 mm. In another aspect of the invention, the pulp fibers may be composed of more than about 50% by weight, low-average fiber length pulp fibers and less than about 50% by weight, high-average fiber length pulp fibers. In that embodiment, the low-average fiber length pulp fibers may have an average length from about 0.8 mm to about 1.1 mm.

In another aspect of the present invention, the liquid transport material may contain up to about 50 percent, by weight, short staple length fibers, including, for example, synthetic fibers, natural fibers, bicomponent fibers and mixtures thereof. In yet another aspect of the invention, the liquid transport material may also contain particulate materials such as, for example, activated charcoal, clay, starch, and hydrocolloid materials commonly referred to as superabsorbent materials.

The liquid transport material may be utilized as a liquid transport component of an absorbent structure which may be part of, for example, a personal care product. In that application, the liquid transport component may have a basis weight ranging from about 10 to about 300 grams per square meter. It is contemplated that even greater basis weights such as for example, up to about 400 or 500 gsm may be used for certain applications. In order to achieve greater basis weights, the liquid transport material may be initially formed as a heavier web or may be formed by combining thinner layers of transport material. Desirably, the liquid transport component of the absorbent structure may have a basis weight ranging from about 35 to about 100 grams per square meter. More desirably, the liquid transport component of the absorbent structure may have a basis weight ranging from about 45 to about 65 grams per square meter.

In another aspect of the present invention, there is provided a process of making a liquid transport material, the process including the steps of: providing a nonwoven fibrous web; superposing the nonwoven fibrous web on a foraminous surface having a mesh of greater than about 60 and a count of greater than about 40; hydraulically needling the nonwoven web at an energy level sufficient to enhance the liquid transport properties of the nonwoven web so that the liquid transport material is adapted to have a liquid transport value of at least 12 grams of liquid per gram of material over 30 minutes; and drying the liquid transport material.

According to the present invention, the nonwoven fibrous web may be provided by depositing an aqueous suspension composed of fibers onto a foraminous surface. Alternatively and/or additionally, the nonwoven fibrous web may be provided by rehydrating a sheet composed of pulp fibers.

Generally speaking, the nonwoven fibrous web is hydraulically needled at a consistency ranging from about 15 to about 35 percent, by weight, solids. The foraminous surface used in the process of the present invention may be a single plane mesh in which both the mesh (i.e., warp yarns of fabric per inch of width) and count (i.e., shute yarns of fabric per inch of length) are greater than 35 and at least one is greater than 50. The foraminous surface may be a multi-ply mesh or perforated plate in which both the effective mesh (i.e., warp yarns of fabric per inch of width) and the effective count (i.e., shute yarns of fabric per inch of length) are greater than 35 and at least one is greater than 50. For example, the foraminous surface may have a mesh size of from about 60×40 to about 200×200. Desirably, the foraminous surface has a mesh size of from about 80×80 to about 100×100.

The drying step utilized in the process may be involve through-air-drying, infra red radiation, yankee dryers, drying cans, microwaves, and ultrasonic energy. In another aspect of the present invention, the drying step may be followed by a mechanical softening step.

DETAILED DESCRIPTION OF THE INVENTION

Figure 1:
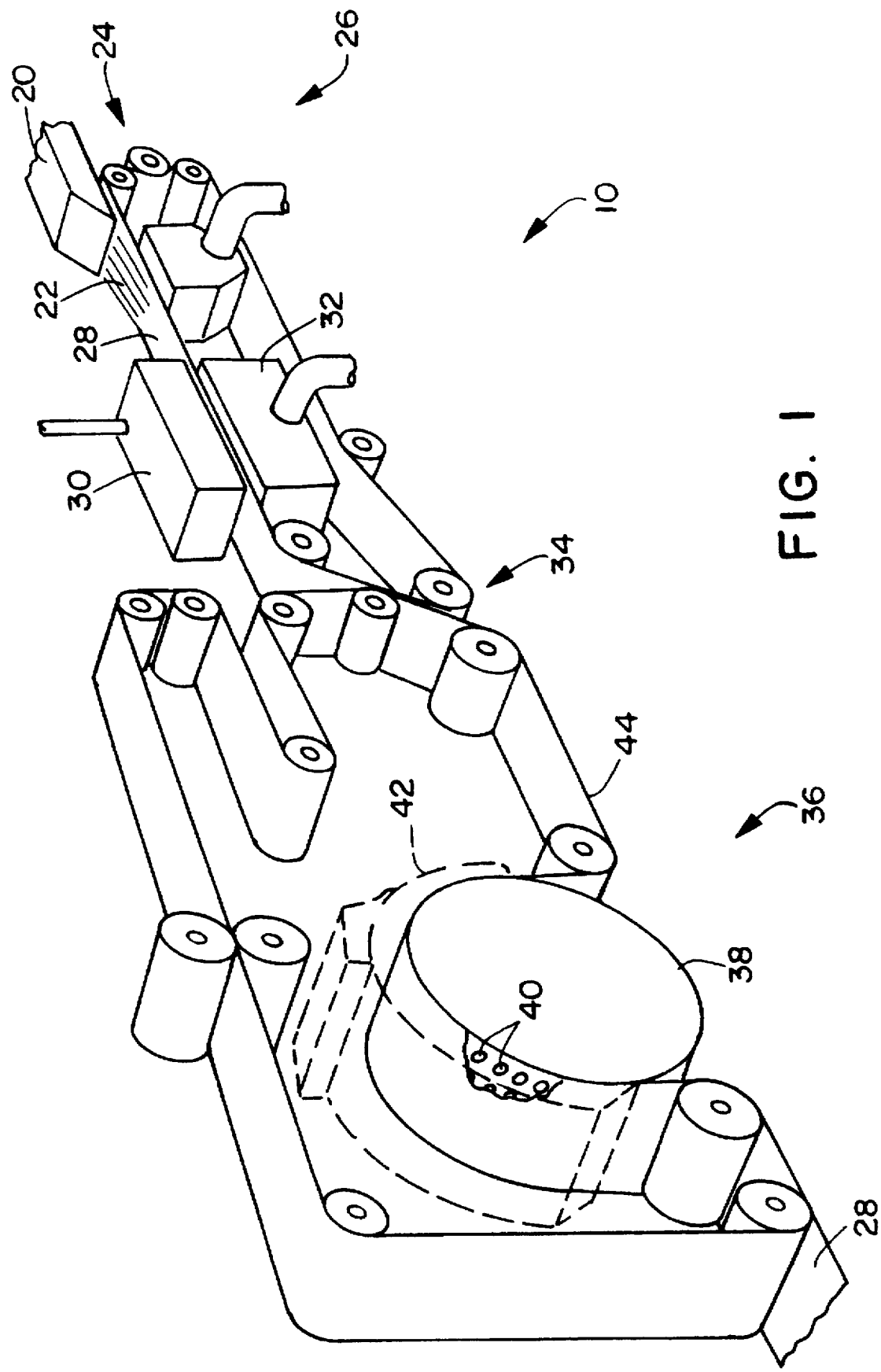
FIG. 1 is an illustration of an exemplary process for making a hydraulically needled liquid transport material.

Referring to FIG. 1 of the drawings there is schematically illustrated at 10 a process for forming a liquid transport material. This liquid transport material is essentially a nonwoven fibrous web which has been hydraulically needled to produce a structure of fibers which efficiently transports liquids. It has been found that the proper combination of hydraulic needling, fiber selection, forming/needling web selection and drying techniques can provide a nonwoven web that takes up, transports and releases liquid to an absorbent material at a rate of at least about 12 grams of liquid per gram of material over 30 minutes.

The nonwoven fibrous web may be made by forming a dilute suspension of fibers, supplying that suspension to a headbox 20 and depositing it via a sluice 22 as a uniform dispersion onto a foraminous screen 24 of a conventional paper-making machine 26. The suspension of fibers may be diluted to any consistency which is typically used in conventional wet-laying processes. For example, the suspension may contain from about 0.02 to about 5 percent by weight fibers suspended in water.

The fibers may be pulp fibers from woody or non-woody plants as well as secondary (i.e., recycled) fiber pulp. Exemplary wood pulps include bleached and unbleached kraft virgin softwood fiber pulps and bleached and unbleached kraft virgin hardwood pulp. Some useful pulps are those available from the Kimberly-Clark Corporation under the trade designations Longlac 19, Longlac 16, Coosa River 55, Coosa River 56, and Coosa River 57. Secondary fiber pulp may be pulp fibers recycled from sources such as, for example, office waste, newsprint, and paperboard scrap. For example, one useful secondary fiber pulp identified as "BJ deinked secondary fiber pulp" is available from Ponderosa Pulp Products—a division of Ponderosa Fibers of America, Atlanta, Ga.

The pulp fibers may be unrefined or may be beaten to various degrees of refinement. Small amounts of wet-strength resins and/or resin binders may be added to improve strength and abrasion resistance. Useful binders and wet-strength resins include, for example, Kymene® 557 H available from the Hercules Chemical Company, and Parez 631 available from American Cyanamid, Inc. Cross-linking agents and/or hydrating agents may also be added to the pulp mixture. Debonding agents may be added to the pulp mixture to reduce the degree of hydrogen bonding if a very open or loose (e.g., softer) nonwoven pulp fiber web is desired. One exemplary debonding agent is available from the Quaker Chemical Company, Conshohocken, Pa., under the trade designation Quaker 2008.

Mixtures of pulp fibers and other types of fibers may also be used. The other fibers may be synthetic fibers, natural fibers, bicomponent fibers, and the like having various deniers and relatively short lengths. For example, short staple length fibers having a length ranging from about 5 mm to about 36 mm may be used. Generally speaking, the nonwoven fibrous web may contain up to about 50 percent, by weight, short staple length fibers. For example, the fibrous component of the hydraulically needled superabsorbent composite materials may contain from about 5 to about 50 percent, by weight, staple length fibers and from about 50 to 95 percent, by weight pulp fibers.

The synthetic fibers may be made from rayon, polyester, polyamides and polyolefins such as, for example, one or more of polyethylene, polypropylene, polybutene, ethylene copolymers, propylene copolymers and butene copolymers. Natural fibers may include, for example, cotton, cotton linters, wool, silk, and flax. Typically, these fibers will have a denier in the range of about 0.7 to about 8 and an average length in the range of about 5 mm to about 36 mm. For example, the fibers may have a denier in the range of about 0.9 to about 3 and an average length in the range of about 10 mm to about 24 mm. As a further example, the fibers may have a denier in the range of about 1 to about 2 and an average length in the range of about 12 mm to about 18 mm.

The suspension of fibers is deposited on the foraminous surface 24 and water is removed to form a uniform nonwoven web of fibers 28. Hydraulic needling may take place on the foraminous surface (i.e., mesh fabric) 24 on which the wet-laid web is formed. Alternatively, the web may be transferred to a different foraminous surface for hydraulic needling. The present invention also contemplates rehydrating a dried fibrous web to a specified consistency and subjecting the rehydrated fibrous web to hydraulic needling.

The nonwoven web 28 passes under one or more hydraulic needling manifolds 30 and is treated with jets of fluid to open up or loosen and rearrange the tight network of fibers. Typically, the hydraulic needling takes place while the nonwoven web is at a consistency between about 15 to about 45 percent solids. For example, the nonwoven web may be at a consistency from about 20 to about 30 percent solids.

According to the invention, the nonwoven fibrous web 28 is hydraulically needled. That is, conventional hydraulic entangling equipment may be operated at conditions which impart relatively low energies (e.g., 0.001 to 0.03 hp-hr/lb) to the web. Water jet treatment equipment which may be adapted to the process of the present invention may be found, for example, in U.S. Pat. No. 3,485,706 to Evans, the disclosure of which is hereby incorporated by reference. The hydraulic needling process of the present invention may be carried out with any appropriate working fluid such as, for example, water. The working fluid flows through a manifold which evenly distributes the fluid to a series of individual holes or orifices. These holes or orifices may be from about 0.003 to about 0.015 inch in diameter. For example, the invention may be practiced utilizing a manifold produced by Honeycomb Systems Incorporated of Biddeford, Me., containing a strip having 0.007 inch diameter orifices, 30 holes per inch, and 1 row of holes. Many other manifold configurations and combinations may be used. For example, a single manifold may be used or several manifolds may be arranged in succession.

In the hydraulic needling process, the working fluid passes through the orifices at a pressures ranging from about 50 to about 1500 pounds per square inch gage (psig) to form fluid streams which impact the nonwoven fibrous web 28, typically with much less energy than found in conventional hydraulic entangling processes. For example, the working fluid passes through the orifices at a pressures ranging from about 50 to about 800 pounds per square inch gage (psig). Desirably, the working fluid passes through the orifices at a pressures ranging from about 75 to about 400 pounds per square inch gage (psig) for fibrous webs containing a predominance of pulp fibers. More entangling energy may be required for high basis weight materials, nonwoven fibrous webs containing large proportions of short staple length fibers, or fibers having a stiffer modulus.

The energy imparted to the nonwoven web by the hydraulic needling process may be expressed in units of horsepower-hours per pound of dry web (hp-hr/lb) and may be calculated utilizing the following equation:

$$\text{Energy} = [0.125((Y * P * Q/(S * B))] * N$$

where:

Y=number of orifices per linear inch of manifold;

P=pressure of the water in the manifold expressed in pounds per square inch gauge (psig);

Q=volumetric flow rate of water expressed in cubic feet per minute per orifice;

S=speed of conveyor passing the web under the water jet streams expressed in feet per minute;

B=weight of pulp fibers treated expressed in ounces per square yard;

N=number of manifold passes.

This energy equation may be found in U.S. Pat. No. 3,485,706, previously incorporated herein by reference, which discusses the transfer of energy from columnar fluid jet streams to a nonwoven fibrous web.

Generally speaking, nonwoven fibrous webs that contain mostly pulp fibers may by hydraulically needled utilizing a fluid pressure ranging from about 60 to about 400 psig, when 1 to 4 manifolds are used. As is typical in many water jet treatment processes, vacuum slots 32 may be located directly beneath the hydro-needling manifolds or beneath the foraminous surface 24 downstream of the entangling manifold so that excess water is withdrawn from the hydraulically-needled nonwoven fibrous web 28.

The hydraulically needled liquid transport material 36 is transferred to a drying operation. A differential speed pickup roll 38 may be used to transfer the web from the hydraulic needling belt to the drying operation. Alternatively, conventional vacuum-type pickups and transfer fabrics may be used. Desirably, the drying operation is a non-compressive drying operation. For example, the web may be non-compressibly dried utilizing a conventional rotary drum through-air drying apparatus shown in FIG. 1 at 40. The through-dryer 40 may be an outer rotatable cylinder 42 with perforations 44 in combination with an outer hood 46 for receiving hot air blown through the perforations 44. A through-dryer belt 48 carries the composite 36 over the upper portion of the through-dryer outer cylinder 42. The heated air forced through the perforations 44 in the outer cylinder 42 of the through-dryer 40 removes water from the transport material 36. The temperature of the air forced through the transport material 36 by the through-dryer 40 may range from about 300° to about 500° F. Other useful through-drying methods and apparatus may be found in, for example, U.S. Pat. Nos. 2,666,369 and 3,821,068, the contents of which are incorporated herein by reference.

It may be desirable to use finishing steps and/or post-treatment processes to impart selected properties to the transport material 36. For example, the web may be mechanically softened. This softening may be accomplished by calendering, perforating, aperturing, perf-embossing, embossing, pattern embossing, differential drawing, creping, and rollers. Softening may also be accomplished by adding debonding agents to the nonwoven fibrous web before or just after the hydraulic needling step. Alternatively and/or additionally, chemical post-treatments may be added to the web such as, for example, adhesives, dyes, surfactants, cross-linking agents, hydrating agents and/or pigments to impart desirable properties such as, for example, abrasion resistance, toughness, color, or improved wetting ability.

Figure 2:
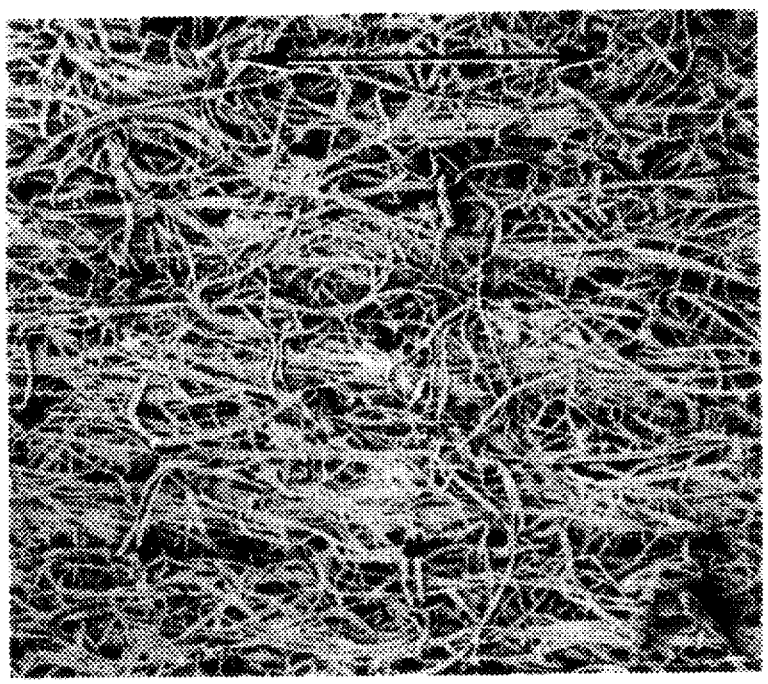
FIG. 2 is a photomicrograph of a surface of an exemplary hydraulically needled liquid transport material.
Figure 3:
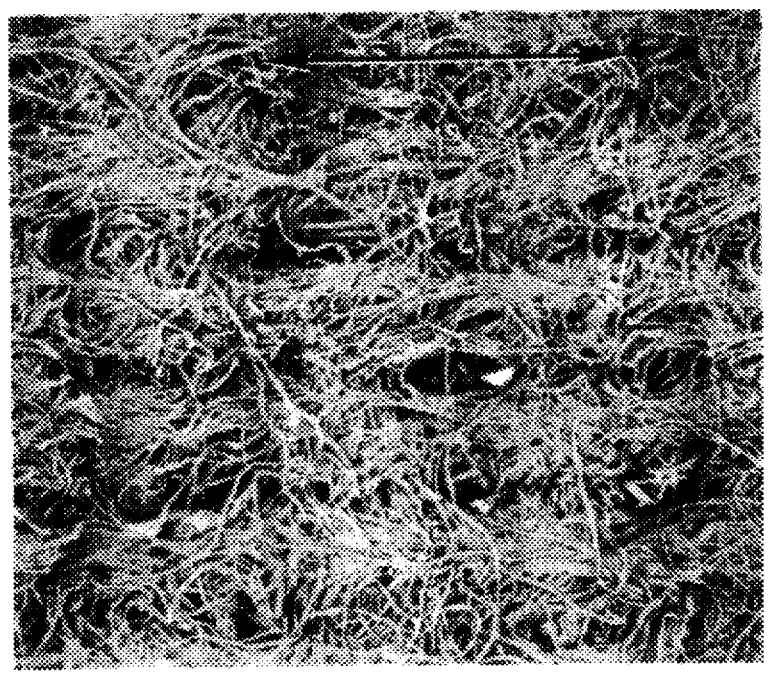
FIG. 3 is a photomicrograph of a surface of an exemplary hydraulically needled liquid transport material.

FIGS. 2 and 3 are 1500× (linear magnification) photomicrographs of the fluid treated surface of exemplary liquid transport materials. Fibers appear to be aligned or oriented across the width of each microphotograph. Additionally, in FIG. 3 the surface has small pores or openings which appear to be aligned or oriented across the width of the photomicrograph. These small pores or openings may range, for example, from about 200 to about 400 microns in diameter.

Figure 4:
FIG. 4 is a photomicrograph of a surface of an exemplary hydraulically needled liquid transport material.
Figure 5:
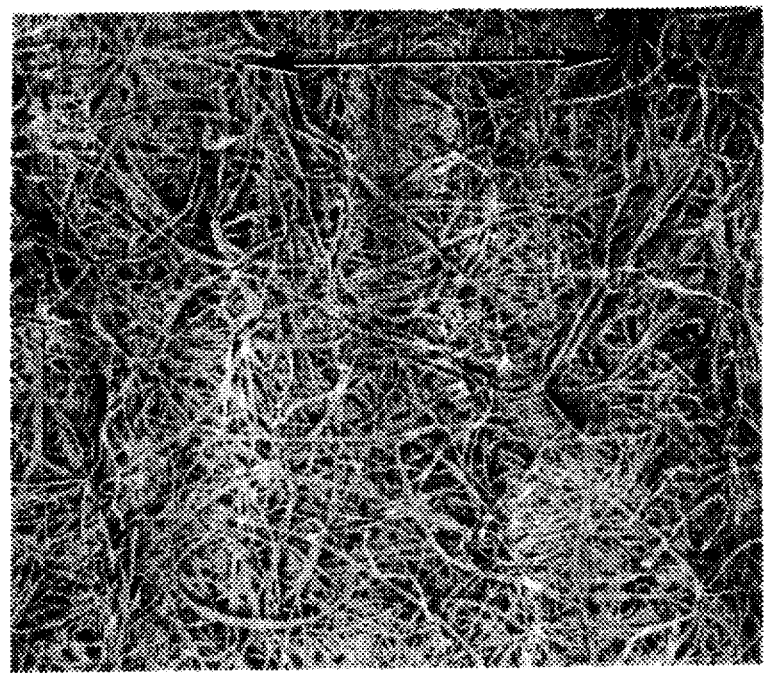
FIG. 5 is a photomicrograph of a surface of an exemplary hydraulically needled liquid transport material.

FIGS. 4 and 5 are 1500× (linear magnification) photomicrographs of the wire side (i.e., the side opposite the fluid treated surface) of exemplary liquid transport materials. Fibers appear to have a quite random or unoriented configuration. No pattern or alignment appears to be visible in either microphotograph.

Although the inventors should not be held to any particular theory of operation, it is believed that opening-up or loosening of the fiber network to provide a relatively uniform series of capillaries, passages or pores along the plane of the nonwoven material enhances the material's ability to pick-up, transport and release liquid as measured by a Distribution/Retention Fluid Test. The particular arrangement of the fiber network is believed to be influenced by the choice of entangling surface as well as the fibers selected for the nonwoven web. Alternatively and/or additionally, the alignment or orientation of fibers along the desired direction of liquid transport also appears to aid in the efficiency of the liquid transport material.

The foraminous surface which is used to make the liquid transport material of the present invention may be a single ply mesh fabric, a multi-ply mesh fabric or perforated plates. In general, the forming fabric must be fine enough to avoid fiber washout and yet allow adequate drainage. The forming fabric should also have a mesh (i.e., warp yarns of fabric per inch of width) of at least about 35 and a count (i.e., shute yarns of fabric per inch of length) of at least about 35. At least one of the mesh or count should be greater than 50. This configuration of mesh and count appears to provide the type of rearrangement and loosening of the pulp fiber network which results in a liquid transport material.

For example, the nonwoven web may be wet laid and hydraulically needled on a conventional single plane mesh in which both the mesh (i.e., warp yarns of fabric per inch of width) and count (i.e., shute yarns of fabric per inch of length) are greater than 35 and at least one is greater than 50. Desirably, the conventional single plane mesh has a mesh size ranging from about 60×40 to about 150×150. More desirably, the conventional single plane mesh has a mesh size ranging from about 80×80 to about 100×100.

The forming fabric may also be a multi-ply mesh. A multiply mesh may be particularly useful when secondary fibers are incorporated into the nonwoven web. If a multi-ply fabric is used, the multi-ply (i.e., compound) fabric may include a coarse layer joined to a fine layer. The coarse layer may be a simple single layer weave. The fine layer may also be another simple single layer weave. The multi-ply mesh or perforated plate should have an effective mesh (i.e., warp yarns of fabric per inch of width) and an effective count (i.e., shute yarns of fabric per inch of length) which is greater than 35 and in which at least one is greater than 50. Desirably, the coarse layer has a mesh (i.e., warp yarns of fabric per inch of width) of at least about 60 and a count (shute yarns of fabric per inch of length) of at least about 40. For example, the coarse layer may have a mesh of about 65 to 80 and a count of about 45 to 60. Generally speaking, the fine layer should have both a mesh and count which is greater than the coarse layer. Desirably the fine layer will have a mesh and count about twice as great as the coarse layer. For example, the fine layer may have a mesh of about 100 and a count of about 100.

Generally speaking, it is desirable for the multi-ply mesh and or perforated plates used in the hydraulic needling process to have an effective mesh size from about 60×40 to about 200×200. More desirably, the multi-ply mesh and or perforated plates have a mesh size ranging from about 80×80 to about 100×100.

If a multi-ply mesh is used during the fluid-jet treatments, the pulp fibers generally conform to the topography of the coarse layer. Flow of fluid through the fabric is controlled by the fine layer on the bottom of the fabric to provide the proper conditions for loosening/opening the pulp fiber network during hydraulic needling while avoiding web break-up, washout of short fibers and intertwining of fibers into the mesh fabric. In some embodiments, the weave patterns may have certain filaments (e.g., warp strands) which protrude to form knuckles. Pulp fibers may be washed off portions of these knuckles to form small pores or openings in the transport material.

Figure 6:
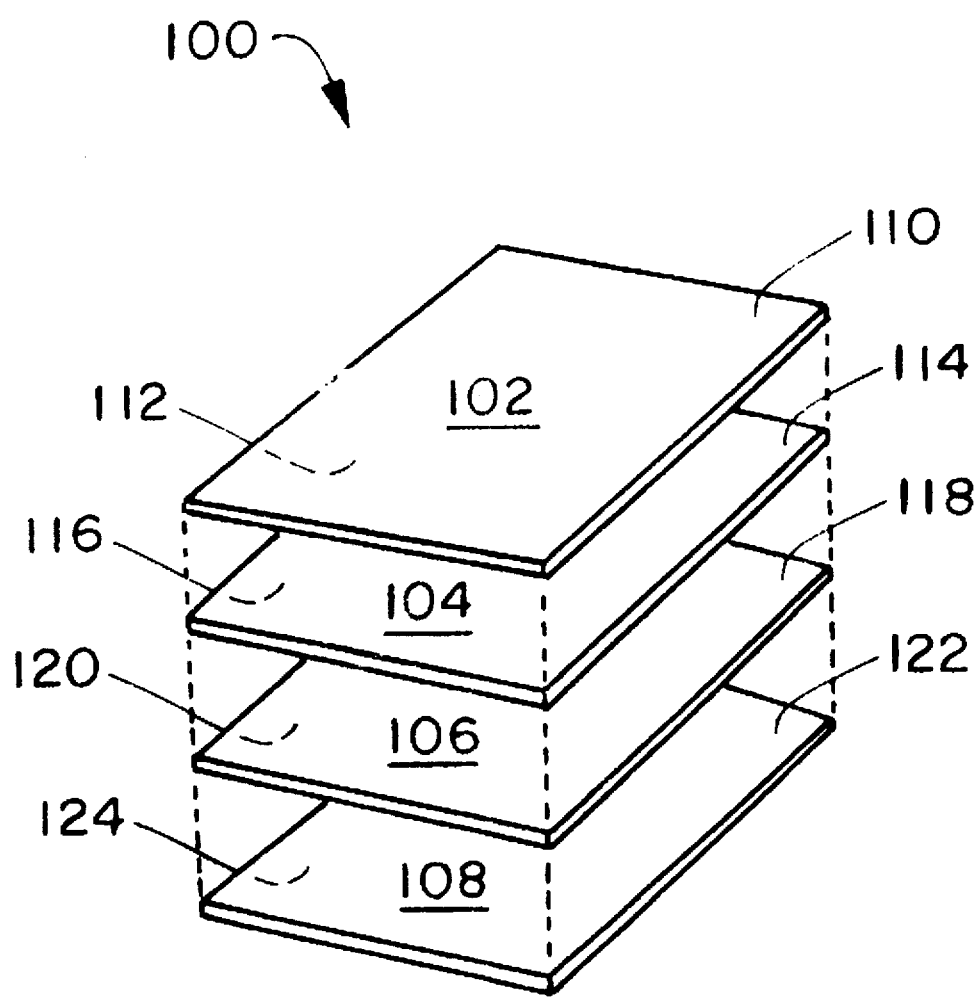
FIG. 6 is a representation of an exemplary absorbent structure that contains a hydraulically needled liquid transport material.

FIG. 6 is an exploded perspective view of an exemplary absorbent structure 100 which incorporates a hydraulically needled liquid transport material. FIG. 6 merely shows the relationship between the layers of the exemplary absorbent structure, and is not intended to limit in any way the various ways those layers (or other layers) may be configured in particular products. The exemplary absorbent structure 100, shown here as a multi-layer composite suitable for use in a disposable diaper, feminine pad or other personal care product, contains four layers: a top layer 102, a liquid transport layer 104, an absorbent layer 106, and a bottom layer 108. The top layer 102 may be a nonwoven web of melt-spun fibers or filaments, an apertured film or an embossed netting. The top layer 102 may function as a liner for a disposable diaper, or a cover layer for a feminine care pad or personal care product. The upper surface 110 of the top layer 102 is the portion of the absorbent structure 100 intended to contact the skin of a wearer. The lower surface 112 of the top layer 102 is superposed on the liquid transport layer 104 which is one or more layers of a hydraulically needled liquid transport material of the present invention. The liquid transport layer 104 serves to rapidly desorb liquid from the top layer 102, evenly distribute liquid throughout the liquid transport layer 104 and quickly release liquid to an absorbent layer 106. The liquid transport layer has an upper surface 114 in contact with the lower surface 112 of the top layer 102. The liquid transport layer 104 also has a lower surface 116 superposed on the upper surface 118 of the absorbent layer 106. The liquid transport layer 104 may have a different size or shape from the absorbent layer 106. Desirably, the absorbent layer 106 is a layer of superabsorbent material and/or mixtures of superabsorbent material and pulp fluff. The absorbent layer 106 is superposed over a fluid-impervious bottom layer 108. The absorbent layer 106 has a lower surface 120 which is in contact with an upper surface 122 of the fluid impervious layer 108. The bottom surface 124 of the fluid-impervious layer 108 provides the outer surface for the absorbent structure 100. In more conventional terms, the liner layer 102 is a topsheet, the fluid-impervious bottom layer 108 is a backsheet, the liquid transport layer 104 is a liquid distribution layer, and the absorbent layer 106 is an absorbent core. Each layer may be separately formed and joined to the other layers in any conventional manner. The layers may be cut or shaped before or after assembly to provide a particular absorbent personal care product configuration.

When the layers are assembled to form a product such as, for example, a disposable diaper, the liquid transport layer 104 formed from one or more layers of the hydraulically needled liquid transport material of the present invention provides the advantages of reducing liquid retention in the top layer, improving liquid transport away from the skin, and more efficient use of the absorbent layer 106 by distributing liquid to a greater portion of the absorbent. These advantages are provided by improved vertical wicking, liquid transport and absorption properties.

As noted above, other absorbent structures are contemplated. For example, an absorbent structure may contain a liner layer, a liquid surge layer (e.g., a resilient bonded, carded web), one or more layers of the hydraulically needled liquid transport material of the present invention, an absorbent core or pulp fluff layer and a fluid-impervious bottom layer. It is contemplated that the liquid transport material could be used to sandwich the absorbent layer. That is, the liquid transport material may be located both above and below the absorbent layer.

One or more layers of the hydraulically needled liquid transport material may be used as a liquid transport material for many products besides disposable personal care products. For example, the absorbent nonwoven composite material may be used as a liquid transport material in food and product packaging, wipers, wound dressings, industrial sorbents, and kennel and catbox liners.

EXAMPLES

Examples 1–10 illustrate exemplary hydraulically needled liquid transport materials. The basis weight, vertical wicking rate, vertical wicking pickup, porosity, mean flow pore size, and distribution/retention fluid test for the materials of Examples 1–11 were measured and are reported in Table 1. The measurements of a material which was formed in the same manner as the other webs but which was not hydraulically needled is reported as Example 11.

Examples 1 and 2

A slurry containing 100% by weight northern softwood unrefined virgin wood fiber pulp (Longlac 19 available from the Kimberly-Clark Corporation) was wet-laid utilizing conventional paper making techniques onto 100×100 single ply mesh fabric. This fabric is generally described as having a mesh of 100 (number of filaments per inch running in the machine direction) and a count of 100 (number of filaments per inch running in the cross-machine direction). The wet-laid web was de-watered to a consistency of approximately 25 percent solids and was hydraulically needled with jets of water at about 200 psig from 2 manifolds each equipped with a jet strip having 0.007 inch diameter holes (1 row of holes at a density of 30 holes per inch). The discharge of the jet orifices were between about 2 cm to about 3 cm above the wet-laid web which travelled at a rate of about 24 feet per minute. Vacuum boxes removed excess water and the treated web was dried utilizing a rotary through-air dryer manufactured by Honeycomb Systems Incorporated of Biddeford, Me.

Example 3

A wet-laid hydraulically needled nonwoven web was formed essentially as described in Example 1 except that the nonwoven web was hydraulically needled on a multi-ply mesh fabric having an effective mesh of 45 (filaments per inch—machine direction) and an effective count of 74 (filaments per inch—cross-machine direction).

Example 4

A wet-laid hydraulically needled nonwoven web was formed essentially as described in Example 1 except that the nonwoven web was hydraulically needled on a single-ply mesh fabric having a mesh of 90 (filaments per inch—machine direction) and a count of 60 (filaments per inch—cross-machine direction). The hydraulic needling took place at a pressure of about 200 psig from 3 manifolds.

Example 5

A wet-laid hydraulically needled nonwoven web was formed essentially as described in Example 2 except that the nonwoven pulp fiber web was hydraulically needled on a single-ply mesh fabric having a mesh of 94 (filaments per inch—machine direction) and a count of 95 (filaments per inch—cross-machine direction). The hydraulic needling took place at a pressure of about 75 psig from 2 manifolds with the nonwoven web passing under the manifolds at a speed of about 750 feet per minute.

Example 6

A wet-laid hydraulically needled nonwoven web was formed essentially as described in Example 2 except that the nonwoven pulp fiber web was hydraulically needled on a single-ply mesh fabric having a mesh of 55 (filaments per inch—machine direction) and a count of 38 (filaments per inch—cross-machine direction). The hydraulic needling took place at a pressure of about 200 psig from 3 manifolds with the nonwoven web passing under the manifolds at a speed of about 24 feet per minute.

Example 7

A wet-laid hydraulically needled nonwoven web was formed essentially as described above except that the web was formed utilizing conventional hand-sheet forming techniques onto a 68×14.5 single ply mesh fabric. This fabric is generally described as having a mesh of 168 (number of filaments per inch running in the machine direction) and a count of 14.5 (number of filaments per inch running in the cross-machine direction). The wet-laid web was de-watered to a consistency of approximately 25 percent solids and was hydraulically needled with jets of water at about 200 psig from 1 manifold. The nonwoven web passed under the manifold 3 times at a speed of about 15 feet per minute.

Example 8

A wet-laid hydraulically needled nonwoven web was formed essentially as described in Example 7 except that the web was formed onto a multi-ply mesh fabric. This fabric is generally described containing a coarse layer having a mesh of 37 (number of filaments per inch running in the machine direction) and a count of 35 (number of filaments per inch running in the cross-machine direction) and a fine layer having a mesh of 74 and a count of 70.

Example 9

A wet-laid hydraulically needled nonwoven web was formed essentially as described in Example 7 except that the web was formed onto a 20×20 single ply mesh fabric. This fabric is generally described as having a mesh of 20 (number of filaments per inch running in the machine direction) and a count of 20 (number of filaments per inch running in the cross-machine direction).

Example 10

A wet-laid hydraulically needled nonwoven web was formed essentially as described in Example 7 except that the web was formed onto a single ply mesh fabric. This fabric is generally described as having a mesh of 30 (number of filaments per inch running in the machine direction) arranged in a twill pattern.

Example 11

A wet-laid nonwoven web was formed essentially as described in Example 1 except that the web was not subjected to hydraulic needling. Vacuum boxes removed excess water and the treated web was dried utilizing a rotary through-air dryer manufactured by Honeycomb Systems Incorporated of Biddeford, Me.

TABLE 1

Hydraulically Needled Pulp Liquid Transport Materials

| Sample ID | Entangling Wire | DRFT (g/g/30 min) | Frazier (cfm/ft$^2$) | Coulter (mfp)* | Vertical Wicking Height (cm) | Vertical Wicking Pickup (g) |
|---|---|---|---|---|---|---|
| 1 | 100 × 100 | 17.88 | 108.70 | 34.00 | 21.5 | 6.0 |
| 2 | 100 × 100 | 19.10 | 91.73 | 33.80 | | |
| 3 | 45 × 74 | 12.45 | 78.41 | 40.62 | | |
| 4 | 90 × 60 | 13.33 | 53.73 | 25.19 | | |
| 5 | 94 × 94 | 12.15 | 87.74 | 44.75 | 22.5 | 3.2 |
| 6 | 55 × 38 | 12.10 | 82.30 | 43.30 | 21.5 | 8.3 |
| 7 | 68 × 14 | 9.50 | 160.80 | 41.49 | 18.0 | 7.2 |
| 8 | 2-ply | 10.50 | 141.50 | 34.63 | 23.5 | 9.7 |
| 9 | 20 × 20 | 10.50 | 182.50 | 38.61 | 18.5 | 7.1 |
| 10 | 30 mesh (twill) | 8.40 | 210.50 | | 17.5 | 6.8 |
| 11 | — | 11.00 | 26.72 | 14.80 | 22.0 | 4.9 |

*Mean flow pore size in microns.

As can be seen in Table 1, the nonwoven materials that were hydraulically needled on a foraminous surface having a mesh of at least about 35 and a count of at least about 35 in which at least one of the two numbers was greater than 50 provided liquid transport values that were at least about 8 percent better than materials treated on coarser wires and/or untreated materials. In some situations, the materials of the present invention provided liquid transport values of 12 to 19 or more grams of liquid per gram of material over 30 minutes.

Materials which are hydraulically needled with coarser fabrics, while exhibiting similar mean flow pore size values (e.g., 25–45 microns), yield sheets having greater Frazier porosity values that the materials of the present invention. As can be seen in Table 1, materials having relatively similar mean flow pore size values but Frazier porosity values of less than about 50 cfm/ft$^2$ or greater than about 140 cfm/ft$^2$ do not transport liquid as effectively as the present invention.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A nonwoven fibrous material comprising a network of pulp fibers that has been loosened and rearranged by treatment with relatively low energy jets of liquid so that the nonwoven fibrous material has a Frazier porosity of from about 50 cfm/ft$^2$ to 91.73 cfm/ft$^2$ and is adapted to absorb, transport and release liquid to an absorbent material at a rate of at least 12 grams of liquid per gram of material over 30 minutes as determined by a Distribution/Retention Fluid Transfer Test.

2. The nonwoven fibrous material according to claim 1 wherein the nonwoven fibrous material is adapted to absorb, transport and release liquid to an absorbent material at a rate of at least 15 grams of liquid per gram of material over 30 minutes as determined by a Distribution/Retention Fluid Transfer Test.

3. The nonwoven fibrous material according to claim 1 wherein the nonwoven fibrous material is adapted to absorb transport and release liquid to an absorbent material at a rate ranging from about 17 to about 25 grams of liquid per gram of material over 30 minutes as determined by a Distribution/Retention Fluid Transfer Test.

4. The nonwoven fibrous material of claim 1 wherein the fibrous nonwoven material has a specific volume ranging from about 8 to about 15 $cm^3/g$.

5. The nonwoven fibrous material of claim 1 wherein the fibrous nonwoven material has a vertical wicking height of at least about 18 cm per 15 minutes.

6. The nonwoven fibrous material of claim 1 wherein the pulp fibers are high-average fiber length pulp fibers.

7. The nonwoven fibrous material of claim 6 wherein the pulp fibers have an average fiber length from about 2 to about 5 mm.

8. The nonwoven fibrous material of claim 1 wherein the pulp fibers comprise more than about 50% by weight, low-average fiber length pulp fibers and less than about 50% by weight, high-average fiber length pulp fibers.

9. The nonwoven fibrous material of claim 8 wherein the low-average fiber length pulp fibers have an average length from about 0.8 mm to about 1.1 mm.

10. The nonwoven fibrous material of claim 1 further comprising up to about 50 percent, by weight, short staple length fibers.

11. The nonwoven fibrous material of claim 10 wherein the short staple length fibers are selected from the group consisting of synthetic fibers, natural fibers, bicomponent fibers and mixtures thereof.

12. The nonwoven fibrous material of claim 1 wherein the nonwoven fibrous material further comprises particulates selected from the group consisting of activated charcoal, clay, starch, and hydrocolloid materials commonly referred to as superabsorbent materials.

13. The nonwoven fibrous material of claim 1 having a basis weight ranging from about 10 to about 300 grams per square meter.

14. The liquid transport component of an absorbent structure according to claim 13, wherein said component has a basis weight ranging from about 10 to about 300 grams per square meter.

15. The liquid transport component of an absorbent structure according to claim 13, wherein said component has a basis weight ranging from about 35 to about 100 grams per square meter.

16. The liquid transport component of an absorbent structure according to claim 13, wherein said component has a basis weight ranging from about 45 to about 65 grams per square meter.

17. A liquid transport component of an absorbent structure wherein the liquid transport component comprises a nonwoven fibrous material composed of a network of pulp fibers that has been loosened and rearranged by treatment with relatively low energy jets of liquid so that the nonwoven fibrous material has a Frazier porosity of from about 50 $cfm/ft^2$ to 91.73 $cfm/ft^2$ and is adapted to absorb, transport and release liquid to an absorbent material at a rate of at least 12 grams of liquid per gram of material over 30 minutes as determined by a Distribution/Retention Fluid Transfer Test.

* * * * *